United States Patent [19]

Kalopissis et al.

[11] 4,035,422
[45] July 12, 1977

[54] 2,6-DIMETHYL-4-SUBSTITUTED AMINO PHENOL COUPLERS

[75] Inventors: Grégoire Kalopissis, Neuilly-sur-Seine; Andrée Bugaut, Boulogne-sur-Seine, both of France; Hubert Gaston-Breton, Tokyo, Japan

[73] Assignee: L'Oreal, Paris, France

[21] Appl. No.: 633,394

[22] Filed: Nov. 19, 1975

Related U.S. Application Data

[60] Continuation-in-part of Ser. No. 302,406, Oct. 31, 1972, abandoned, which is a division of Ser. No. 848,329, Aug. 7, 1969, Pat. No. 3,712,790.

[30] Foreign Application Priority Data

Aug. 14, 1968 Luxembourg .......................... 56722

[51] Int. Cl.² .............. C07C 103/29; C07C 103/38; C07C 91/44; C07C 91/30
[52] U.S. Cl. ...................... 260/559 A; 260/562 A; 260/570.5 P; 260/573; 260/574
[58] Field of Search .... 260/559 A, 562 R, 570.5 P, 260/573, 574, 575, 570.7, 562 A; 8/10.2, 11

[56] References Cited

U.S. PATENT DOCUMENTS

| 1,920,828 | 8/1933 | Wyler ................................. 260/562 |
| 2,642,397 | 6/1953 | Morway et al. ........... 260/562 A X |
| 3,492,349 | 1/1970 | Doyle et al. ..................... 260/562 A |
| 3,558,259 | 1/1971 | Kalopissis et al. ..................... 8/10.2 |
| 3,563,684 | 2/1971 | Charle et al. ............................ 8/11 |
| 3,591,323 | 7/1971 | Kalopissis et al. ............. 260/575 X |
| 3,811,831 | 5/1974 | Bugaut et al. ............................ 8/11 |
| 3,834,866 | 9/1974 | Pum ........................................ 8/11 |

OTHER PUBLICATIONS

Kinesch et al., Monat. Chem., vol. 96, pp. 1315–1323 (1965).
Corbett, Chap. VII (Hair Dyes), *The Chemistry of Synthetic Dyes*, Venkatareman, Ed., vol. 5, Academic Press (1971), pp. 478–483.

Primary Examiner—Daniel E. Wyman
Assistant Examiner—Thomas A. Waltz
Attorney, Agent, or Firm—Cushman, Darby & Cushman

[57] ABSTRACT

Oxidation dye coupling compound, for use in dyeing live human hair, having the formula:

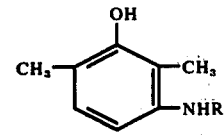

(I)

wherein R is lower alkyl having 1–6 carbon atoms, hydroxyalkyl having 1–6 carbon atoms, acetyl, propionyl, amino alkyl wherein the alkyl moiety has 1–6 carbon atoms, N-dialkylated amino alkyl wherein each of the alkyl moieties has 1–6 carbon atoms and carbamyl methyl.

2 Claims, No Drawings

2,6-DIMETHYL-4-SUBSTITUTED AMINO PHENOL COUPLERS

This application is a continuation-in-part of our application Ser. No. 302,406, filed Oct. 31, 1972, now abandoned, which is a division of our application Ser. No. 848,329, filed Aug. 7, 1969, now U.S. Pat. No. 3,712,790.

Certain conventional methods of dyeing keratinic fibers and particularly human hair comprise the application thereto of dyeing compositions which contain oxidation dyes and in particular aromatic ortho or para diamines and ortho or para aminophenols, which are generally referred to as "oxidation bases". The shade obtained with these bases may be varied by using color modifiers or "couplers", and in particular aromatic meta diamines or meta aminophenols.

An object of the present invention is to provide a new class of couplers which may be utilized with known oxidation dyes.

The present invention is directed to new oxidation dye coupling compounds which have the formula:

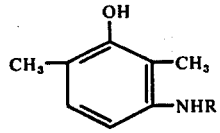
(I)

wherein R is selected from the group consisting of lower alkyl having 1–6 carbon atoms, hydroxyalkyl having 1–6 carbon atoms, acetyl, propionyl, amino alkyl wherein the alkyl moiety has 1–6 carbon atoms, N-dialkylated amino alkyl wherein each of the alkyl moieties has 1–6 carbon atoms and carbamyl methyl.

The N-acyl compounds can be prepared by reacting the corresponding acid anhydride on 3-amino-2, 6-dimethyl phenol, which, in turn, can be prepared by reducing the corresponding nitro compound by using iron in an acetic acid medium as the reducing agent. The compounds of formula I in which R represents an alkyl, hydroxyalkyl, amino alkyl, or carbamyl methyl radical can be obtained by reacting a suitably selected halogenated derivative on 3-amino-2, 6-dimethyl phenol.

Another object of the invention is to provide a new composition for dyeing keratinic fibers, and in particular live human hair, which is essentially characterized by the fact that it contains, in association with at least one conventional oxidation base, at least one compound having the above formula I.

Among the illustrative oxidation bases which may be used in association with the couplers of formula I are: paraphenylenediamine, paratoluylene-diamine, para-aminophenol, N-methyl-para-aminophenol, chloro-para-phenylenediamine, methoxy-para-phenylene-diamine, 6-methoxy-3-methylpara-phenylene-diamine, (N-ethyl, N-carbamyl-ethyl)-paraphenylene-diamine, and 2,5-diamino-pyridine.

Among the illustrative couplers of formula I are 3-acetylamino-2,6-dimethyl-phenol and 3-carbamylmethylamino-2,6-dimethyl-phenol.

These new couplers produce particularly stable colors within the blue to red range when associated with oxidation bases. Further, the 2,6-dimethyl-3-NHR phenols of the present invention exhibit significantly greater stability in an alkaline medium, particularly an NaOH medium and significantly improve solubility characteristics in water-ethanol mixtures, then corresponding mono-methyl substituted compounds.

In the dyeing composition of the invention, the base to coupler ratio may vary within broad limits but there is preferably an excess of coupler.

The dyeing composition of this invention may also contain other dyes suitable for use under the same conditions, such as direct dyes, for example azo or anthraquinone dyes, or dyes obtained by associating bases and couplers other than those which constitute the subject matter of the present invention.

The compositions of this invention may also contain wetting agents, dispersing agents, penetrating agents, or other ingredients conventionally used in the dyeing of hair. They may take the form of an aqueous solution, an aqueous-ethanolic solution, a cream or a gel.

The dyeing compositions of this invention are used in a conventional manner at an alkaline pH, preferably between 8 and 10, this pH being obtained by addition of, for example, ammonia, and they are applied to the hair in the presence of an oxidizing solution, which is preferably a hydrogen peroxide solution.

It is a further object of the present invention to provide a new method of dyeing hair which is characterized by the fact that after having made it alkaline by aid of, for example NaOH or ammonia, hydrogen peroxide is added to a dyeing composition such as the one described above and the resulting mixture is applied to the hair. The hair is then rinsed, shampooed and dried.

The following examples illustrate the different forms of the invention. The percentages mentioned in these examples are by weight, and the temperatures are indicated in degrees centigrade.

EXAMPLES OF PREPARATION

EXAMPLE 1

Preparation of 3-acetylamino-2,6-dimethyl-phenol 39.7 g (0.29 mole) of 3-amino-2,6-dimethyl-phenol are dissolved in 200 cm$^3$ of boiling water. 41 g (0.5 mole) of acetic anhydride are then added to this solution. The reaction mixture is kept in a boiling water bath for 10 minutes, cooled, and dried, thus yielding 40 g of 3-acetyl amino-2,6-dimethyl phenol in practically pure form which, after recrystallization in ethyl acetate, melts at 158°.

EXAMPLE 2

Preparation of 3-propionylamino-2,6-dimethyl phenol 4.5 g (0.03 mole) of 3-amino-2,6-dimethyl phenol are dissolved in 30 cm$^3$ of ethyl acetate. 4 cm$^3$ of propionic anhydride are added and the mixture heated at reflux for 30 minutes. After cooling, drying yields 4.4 g of 3-propionylamino-2,6-dimethyl phenol which after recrystallization in ethyl acetate, melts at 140°.

EXAMPLE 3

Preparation of 3-carbamylmethylamino-2,6-dimethyl phenol 10.96 g (0.08 mole) of 3-amino-2,6-dimethyl phenol and 7.7 g (0.082 mole) of chloroacetamide are dissolved in 66 cm$^3$ of a 50-50 mixture of ethanol and water which has been heated to reflux. 5.6 g of calcium carbonate in suspension in 12 cm$^3$ of water are then added, and reflux is continued for 4 hours. The boiling liquid is then filtered. After cooling the filtrate, drying yields 10.4 g of 3-N-carbamylmethylamino2,6-dimethyl phenol which, after recrystallization in ethanol, melts at 159°.

The 3-amino-2,6-dimethyl phenol employed in the above examples can be prepared as follows:

EXAMPLE 4

Preparation of 3-amino-2,6-dimethyl phenol 157 g (0.94 mole) of 2,6-dimethyl-3-nitro phenol is added little by little, while stirring, to a reducing mixture consisting of 950 cm$^3$ of water, 30 cm$^3$ of acetic acid and 158 g of iron, which has first been heated to 70°. When this addition has been completed, the heating is continued for 20 minutes. The reaction mixture is then neutralized with sodium carbonate and the boiling liquid is filtered. After cooling the filtrate, drying yields 80 g of 3-amino-2,6-dimethyl phenol which, after recrystallization in benzene, melts at 104°.

| Analysis | Calculated for $C_8H_{10}ON$ | Found |
|---|---|---|
| C % | 70.07 | 70.03 |
| H % | 8.03 | 7.98 |
| N % | 10.22 | 10.00 – 10.20 |

EXAMPLES OF APPLICATION
Example 5

| The following dyeing solution is prepared: | |
|---|---|
| 3-N-carbamylmethylamino-2,6-dimethyl-phenol | 0.485 g |
| paratoluylene diamine | 0.3 g |
| 20% ammonium lauryl sulfate (aqueous ammonium lauryl sulfate solution, the concentration of which is 20% as referred to lauryl alcohol) | 20 g |
| Ethylene diamino tetra-acetic acid | 0.3 g |
| 20% ammonia | 10 g |
| 40% sodium bisulfite | 1 g |
| Water, q.s.p. | 100 g |

When this solution is mixed with an equal weight of 6% hydrogen peroxide and applied for 30 minutes to 100% white hair, a violine color is produced.

Example 6

| The following dyeing solution is prepared: | |
|---|---|
| 3-propionylamino-2,6-dimethyl-phenol | 0.482 g |
| Paratoluylene diamine | 0.3 g |
| 20% lauryl ammonium sulfate | 20 g |
| Ethylene diamino tetra-acetic acid | 0.3 g |
| 20% ammonia | 15 g |
| 40% sodium bisulfite | 1 g |
| Water, q.s.p. | 100 g |

When this solution is mixed with an equal weight of 6% hydrogen peroxide and applied for 30 minutes to 100% white hair, a blue gray color is produced.

Example 7

| The following dyeing solution is prepared: | |
|---|---|
| Paratoluylene diamine | 1 g |
| 3-acetylamino-2,6-dimethyl-phenol | 1.3 g |
| 20% lauryl ammonium sulfate | 20 g |
| Ethylene diamino tetra-acetic acid | 0.3 g |
| 20% ammonia | 10 g |
| 40% sodium bisulfite | 1 g |
| Water, q.s.p. | 100 g |

When this solution is mixed with an equal weight of 6% hydrogen peroxide and applied for 30 minutes to 100% white hair, a violet blue shade is produced.

Example 8

| The following dyeing solution is prepared: | |
|---|---|
| 3-acetylamino-2,6-dimethyl-phenol | 1 g |
| Para-aminophenol | 1.5 g |
| 20% lauryl ammonium sulfate | 20 g |
| Ethylene diamino tetra-acetic acid | 0.3 g |
| 20% ammonia | 10 g |
| 40% sodium bisulfite | 1 g |
| Water, q.s.p. | 100 g |

When this solution is mixed with an equal weight of 6% hydrogen peroxide and applied for 30 minutes to 100% white hair, a reddish blond color results.

Example 9

| The following dyeing solution is prepared: | |
|---|---|
| Paratoluylene diamine | 1 g |
| 3-acetylamino-2,6-dimethyl-phenol | 1 g |
| Resorcinol | 1.5 g |
| 3-methoxy-2,6-dimethyl-paraphenylene diamine dihydrochloride | 2.5 g |
| 4-γ-aminopropylamino-1-methylamino-anthraquinone | 1 g |
| 20% lauryl ammonium sulfate | 20 g |
| Ethylene diamino tetra-acetic acid | 0.3 g |
| 20% ammonia | 10 g |
| 40% sodium bisulfite | 1 g |
| Water, q.s.p. | 100 g |

When this solution is mixed with an equal weight of 6% hydrogen peroxide and applied for 30 minutes to 100% white hair, a bluish black shade results.

The oxidation dye coupler compositions of this invention may be placed in any suitable carrier such as water, alcohol, etc., and they may be in any suitable form such as solution, gel, cream, aerosol, etc. Suitable carriers, gelling agents, aerosol compositions, etc., are set forth in many textbooks, such as Cosmetic Compositions Vol. I and II by Harry.

Illustrative coupling compounds of this invention are:

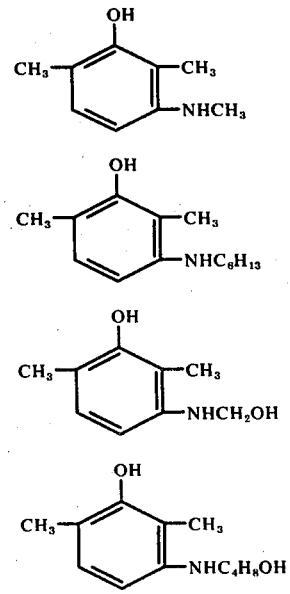

-continued

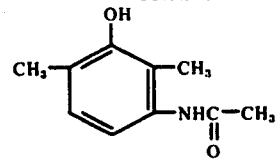

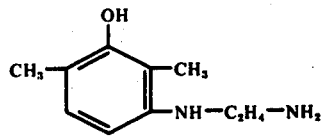

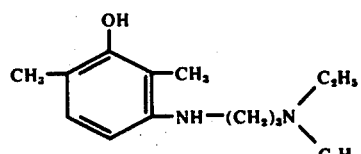

What is claimed is:
1. A compound of the formula

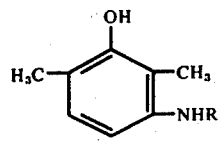

wherein R is selected from the group consisting of lower alkyl having 1–6 carbon atoms, hydroxyalkyl having 1–6 carbon atoms, acetyl, propionyl, amino alkyl wherein the alkyl moiety has 1–6 carbon atoms, N-dialkylated amino alkyl wherein each of the alkyl moieties has 1–6 carbon atoms and carbamyl methyl.

2. The compound of claim 1 selected from the group consisting of 3-acetylamino-2,6-dimethyl phenol, 3-carbamylmethylamino-2,6-dimethyl phenol and 3-propionylamino-2,6-dimethyl phenol.

* * * * *